(12) United States Patent
Martin

(10) Patent No.: US 11,298,514 B2
(45) Date of Patent: Apr. 12, 2022

(54) FOAM APPLICATOR FOR IN-EAR USE

(71) Applicant: Roy J. Martin, Sugar Grove, IL (US)

(72) Inventor: Roy J. Martin, Sugar Grove, IL (US)

(*) Notice: Subject to any disclaimer, the term of this patent is extended or adjusted under 35 U.S.C. 154(b) by 291 days.

(21) Appl. No.: 16/665,681

(22) Filed: Oct. 28, 2019

(65) Prior Publication Data

US 2020/0061356 A1 Feb. 27, 2020

Related U.S. Application Data

(62) Division of application No. 15/322,150, filed on Dec. 26, 2016, now abandoned.

(51) Int. Cl.
| | | |
|---|---|---|
| *A61M 31/00* | (2006.01) | |
| *A61M 11/00* | (2006.01) | |
| *A61F 11/00* | (2022.01) | |

(52) U.S. Cl.
CPC ............ *A61M 31/00* (2013.01); *A61F 11/00* (2013.01); *A61M 11/007* (2014.02); *A61M 11/008* (2014.02); *A61M 2210/0662* (2013.01)

(58) Field of Classification Search
CPC ............ A61M 11/007; A61M 11/008; A61M 2210/0662; A61M 2210/0668; A61M 2210/0675; A61M 2250/00; A61M 31/00; A61F 11/00; A61F 11/006
See application file for complete search history.

(56) References Cited

U.S. PATENT DOCUMENTS

| | | | |
|---|---|---|---|
| 823,499 A * | 6/1906 | Barlow | A61F 13/2051 |
| | | | 604/286 |
| 3,471,064 A | 10/1969 | Micallef | |
| 3,749,083 A | 7/1973 | Mathes, Jr. et al. | |
| 3,990,448 A * | 11/1976 | Mather | A61M 3/0279 |
| | | | 604/275 |
| 5,176,654 A | 1/1993 | Schreiber | |
| 6,505,986 B1 | 1/2003 | Oder | |
| 6,949,088 B2 * | 9/2005 | Macrae | A61F 11/002 |
| | | | 604/275 |
| 8,430,107 B2 | 4/2013 | Huang | |
| 8,956,333 B2 * | 2/2015 | Vlodaver | A61F 11/00 |
| | | | 604/257 |
| 2011/0066172 A1* | 3/2011 | Silverstein | A61F 13/38 |
| | | | 606/162 |

(Continued)

FOREIGN PATENT DOCUMENTS

| | | |
|---|---|---|
| EP | 0176608 A1 | 4/1986 |
| GB | 2237743 A | 5/1991 |

(Continued)

*Primary Examiner* — Quynh-Nhu H. Vu
(74) *Attorney, Agent, or Firm* — Depeng Bi; The Law Offices of Konrad Sherinian LLC

(57) ABSTRACT

A device for dispensing a foam medication into a human or animal ear includes a supply of foamable medicine held within a container. The medicine is advanced through a delivery tube that is configured to engage an ear without entering the ear canal to an extent that it contacts the eardrum. The delivery tube has an enlarged end portion that prevents the device from being inserted too far into an ear, and the enlarged end portion has a series of openings oriented in two different directions to deliver foam into the ear forward of the device and around the circumference of the delivery tube.

12 Claims, 5 Drawing Sheets

(56) References Cited

U.S. PATENT DOCUMENTS

2011/0224625 A1* 9/2011 Flickinger ......... A61M 25/0068
604/257
2011/0297240 A1  12/2011 Fanelli et al.
2011/0311462 A1* 12/2011 Eilat ................... A61K 9/0046
424/45

FOREIGN PATENT DOCUMENTS

WO  WO2005011875 A2  2/2005
WO  WO2009132223 A1  10/2009

* cited by examiner

FOAM APPLICATOR FOR IN-EAR USE

REFERENCE TO RELATED APPLICATIONS

This application is a divisional patent application of co-pending U.S. patent application Ser. No. 15/322,150, entitled "FOAM APPLICATOR FOR IN-EAR USE," filed Dec. 26, 2016, which is hereby incorporated by reference in its entirety, and which is a National Stage entry from PCT Application Number PCT/US2015/041229, entitled "FOAM APPLICATOR FOR IN-EAR USE," filed Jul. 21, 2015, which claims priority of prior U.S. provisional patent application No. 62/026,737, filed Jul. 21, 2014, which is incorporated by reference in its entirety.

BACKGROUND OF THE DISCLOSURE

The present disclosure relates generally to dispensers for dispensing solutions into an ear canal and more particularly, to an improved dispenser that is utilized with a foam solution to reliably deliver the solution into an ear canal of a human or animal subject.

The ear is an important organ to the human body as it not only provides hearing, but also importantly provides balance. A human ear consists of three portions: the outer ear, the middle ear, and the inner ear. These three ear portions cooperatively function together to convert sound waves into nerve impulses that travel to the brain, where they are perceived as sound. The inner ear portion maintains balance. Three ear portions are also present in animals, albeit in longer or shorter lengths than in a human ear.

The outer ear consists of the external part of the ear and the car canal. Part of it is cartilage covered by skin and is shaped to capture sound waves and funnel them through the ear canal to the eardrum. The eardrum is a thin, sensitive membrane that separates the outer ear from the middle ear. The middle ear consists of the eardrum and a small air-filled chamber containing tiny bones that connect the eardrum to the inner car. An Eustachian tube is a small tube that connects the middle ear with the back of the nose and allows outside air to enter the middle ear. The Eustachian tube opens when a person swallows, and helps maintain equal air pressure on both sides of the eardrum in order to prevent fluids from accumulating in the middle ear. If the air pressure on both sides of the eardrum is not equal, the eardrum may bulge or retract, which can be uncomfortable and distort hearing. Upper respiratory infections and common colds inflame and block the Eustachian tube, which may lead to middle ear infections or changes in the pressure of the middle ear pressure, causing ear pain.

The inner ear is a complex labyrinthine structure that includes the cochlea, the organ of hearing and the vestibular system, the organ of balance. The cochlea is filled with fluid and small hairs, known as cilia, that extend into the fluid. Sound vibrations transmitted from the ossicles in the middle ear to the oval window in the inner ear cause the fluid and cilia to vibrate and convert the vibrations into nerve impulses which are transmitted to the brain. It can therefore be understood that problems with the ears may affect both the hearing and balance of the car's subject.

Many diseases and ear problems are treated by way of liquid ear drops. Generally, ear drops are based on antibiotic agents, antibacterial agents, antifungal agents, antiviral agents, steroid derivatives, anti-inflammatory agents, analgesic compounds or a mixture thereof. Ear drops are usually administered to the treated ear by tilting the head of a subject to the side, injecting drops of the medication into the ear and maintaining the subject's head in its tilted position for few minutes in order to allow the medication travel inside the ear and to reach at least the far end of the ear canal. A clean cotton plug is inserted into the ear opening to prevent the medication from leaking out. In order to prevent contamination of the ear drops, the bottle tip must not be contacted by any surface, including the hands and the ear itself.

There are drawbacks associated with ear drops. Ear drops provide treatment by direct contact with the affected area, so that the administration of the ear drops is incorrect, such as if the subject's head is not tilted for a sufficient time, the ear drops will not reach the infected area(s). In animals, such as dogs, the ear canal has a defined initial vertical canal that is joined to a subsequent and adjacent horizontal canal in which the ear drum is located. An animal's head tends to move during delivery, making it difficult to direct medication in both the vertical and horizontal canals. With a single opening, an ear drop device is capable of delivering medication only in one direction in the ear canal. The delivery of ear drops can also be impaired in a number of different ways, including the drops not entering the ear canal or the animal horizontal canal, a too short period of contact with the affected surface(s) of the car if the drops are naturally washed out or because the subject's head is not tilted long enough for the medication to make contact with the affected area(s). Ear drops are difficult to apply to small children and animals that cannot maintaining a stationary position for a few minutes. It is possible that cotton plugs added to the ear after injecting the car drops can become pushed inside the ear canal and difficult to remove.

One device for delivering medication into the ear canal is described in U.S. Pat. No. 6,764,470 which uses a flexible, hollow casing that is inserted into the ear. It is squeezed to break an internal barrier at its distal end that defines an inner reservoir for a medication to release and push the medication into the car. The casing fits in the ear, and it injects the medication when squeezed. This device is awkward for use with infants and small children as well as animals. The overall configuration of this device is cylindrical and the risk exists that it may be pushed too far into the ear, resulting in either bruising or puncturing of the eardrum. Also, as it has only one opening, it can only deliver the medication in one direction within the ear canal.

The present disclosure is therefore directed to an ear medication delivery device that is easy to use and which overcomes the aforementioned disadvantages, and which is particularly suitable for use with animals.

SUMMARY OF THE PRESENT DISCLOSURE

Accordingly, there is provided a medication applicator that is suitable for beneficially delivering an amount of medication in a foam state, into a subject's ear canal, whether human or animal.

In accordance with an embodiment as described in the following disclosure, a foam dispensing apparatus particularly suitable for ear medication applications may include a flexible container that is squeezable by the person applying the foam. The container has a neck portion that engages a cap and the cap includes a bore that receives an elongated application tube therethrough. The application tube has an opening at a base end thereof that is submerged at an level beneath the level of a liquid solution held within the container. The base end opening may be configured to provide a specific flowpath that encourages the production of foam or it may have a standard, tubular opening.

The application tube terminates at its other end in a delivery end. The delivery end is spaced apart from the cap a preselected distance so that the delivery end may be introduced into a subject's ear, but the container is disposed a comfortable distance outside of the ear so that it does not collide with the subject during application. In an important aspect of the present disclosure, the delivery end has a plurality of openings formed therein that define a like plurality of flow passages through the application tube. The openings may be randomly arranged at the delivery end, but it is preferred that they be arranged in at least a radial pattern along with some openings in a longitudinal direction is most preferred and other openings arranged in circular arrays surrounding the opening of the longitudinal axis and of increasing radius. Still other patterns of the openings may include at least one axial opening so that foam may be injected in an axial direction in the ear canal, and with one or more circumferential rows of radial openings disposed rearwardly of the axial opening.

The delivery end of the application tube may include an enlarged end portion that utilize one of a variety of configurations including ones that are bulb-shaped, bulbous or the like or ones that have one or more projections extending radially outwardly therefrom that define a stop surface, or shoulder, that has a general preselected diameter larger than that of an ear canal so that the insertion length of the application tube is maintained at a distance less than that which would contact the ear drum of the subject. The enlarged end portions ends may also include a small axial extension to position and direct the axial opening further down in the ear canal during usage. In a preferred embodiment, the projection, or enlarged end, has a preselected length related to its diameter so that it will fit properly in the ear canal.

These and other objects, features and advantages of the present disclosure will be clearly understood through a consideration of the following detailed description.

BRIEF DESCRIPTION OF THE DRAWINGS

The organization and manner of the structure and operation of the disclosure, together with further objects and advantages thereof, may best be understood by reference to the following detailed description, taken in connection with the accompanying Figures, wherein like reference numerals identify like elements, and in which:

FIG. 3A-1 is a perspective view of a first embodiment of a delivery tip for an applicator tube suitable for use with the ear medication applicator of FIG. 1;

FIG. 3A-2 is a diagrammatic view of a radial opening pattern utilized in the delivery tip of FIG. 3A-1;

FIG. 3B-1 is a perspective view of a second embodiment of a delivery tip for an applicator tube suitable for use with the ear medication applicator of FIG. 1:

FIG. 3B-2 is an elevational view of the distal end of the delivery tip of FIG. 3B-1;

FIG. 3C-1 is a perspective view of a third embodiment of a delivery tip for an applicator tube suitable for use with the ear medication applicator of FIG. 1;

FIG. 3C-2 is a side elevational view, partly in section, of the delivery tip of FIG. 3C-1;

DETAILED DESCRIPTION OF THE DISCLOSURE

While the present disclosure may be susceptible to embodiment in different forms, there is shown in the Figures, and will be described herein in detail, specific embodiments, with the understanding that the disclosure is to be considered an exemplification of the principles of the present disclosure, and is not intended to limit the present disclosure to that as illustrated.

In the illustrated embodiments, directional representations—i.e., up, down, left, right, front, rear and the like, used for explaining the structure and movement of the various elements of the present disclosure, are relative. These representations are appropriate when the elements are in the position shown in the Figures. If the description of the position of the elements changes, however, it is assumed that these representations are to be changed accordingly.

Figure 1:
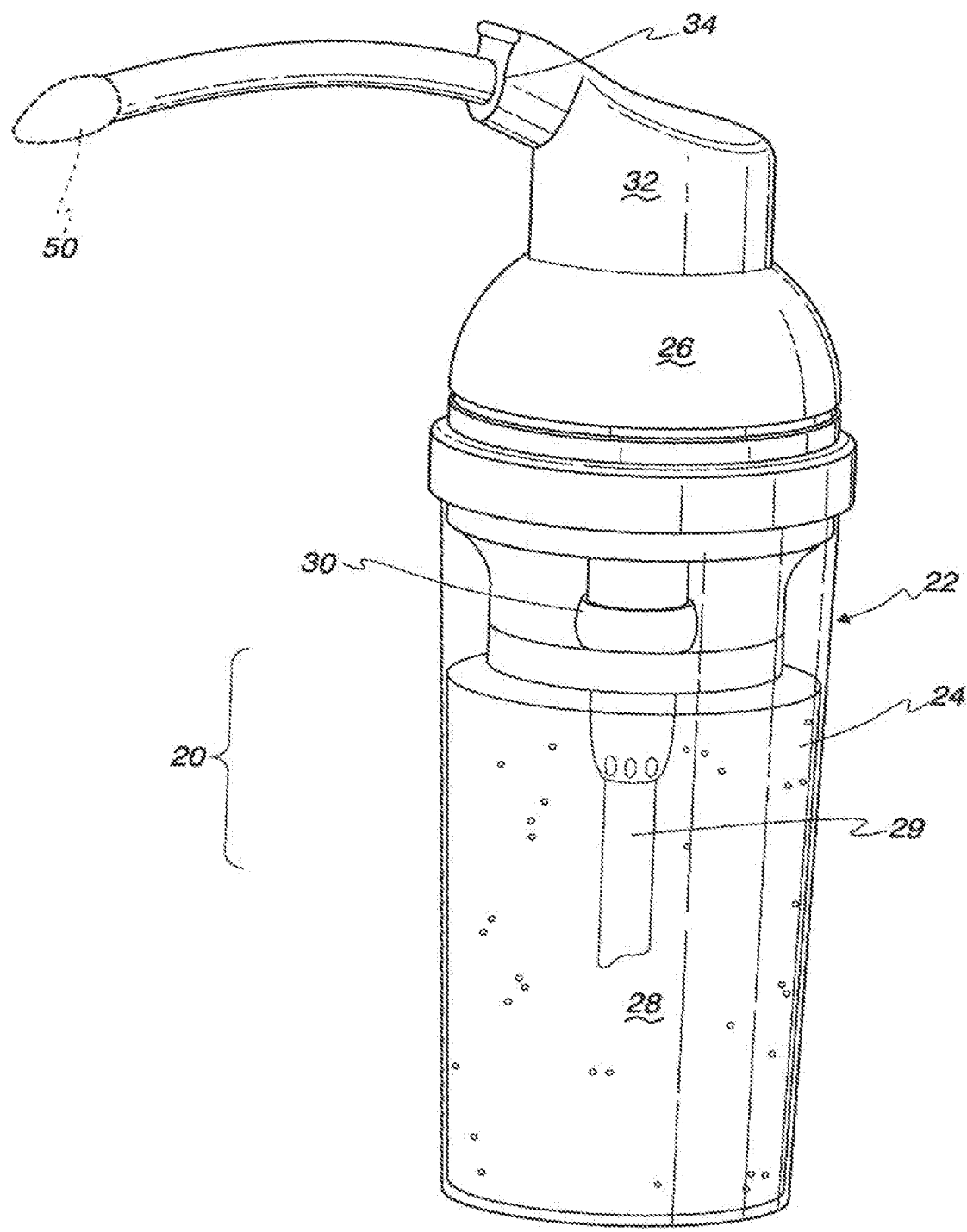
FIG. 1 illustrates a perspective of a ear medication application apparatus constructed in accordance with the principles of the present disclosure.

FIG. 1 illustrates an ear medication delivery device 20 in the form of a hollow container 22 that has a hollow, cylindrical body portion 24 and an interengaging cover, or cap portion, 26 each of which are preferably threaded to engage each other in a twist on and twist off fashion. The body portion 24 provides a hollow reservoir for a medication, illustrated in FIG. 1 as a liquid solution 28. An internal pump 30 is provided to dispense the solution 28 in the form of a foam by way of a delivery tip 50, shown in phantom in FIG. 1, from the solution 28 by way of a supply tube 29 extending below the level of the solution 28 in the container 22. The pump 30 may have an actuator head 32 with a nozzle 34 integrally formed therewith or as part of an overall mechanism. The actuator head 32 may be movably mounted on the container cap portion 26 so that it is capable of reciprocal movement in a vertical direction so that it may be operated in a push-down, pop-up fashion.

Alternatively, the device 20 may take the form of a squeeze bottle 36 with an internal mechanism that permits the entrance of air into the container 20 so that air may contact the liquid solution by way of vents 37 and/or a one-way air valve 38 for the purpose of converting the liquid solution into a dispensable foam. Typically, air can be introduced into the container by pulling up on the head or nozzle assembly of the device. Once inside the container, when the body of the container is squeezed, the air will mix with the liquid and form a foam in the area between the interior of the container and the nozzle, including the applicator tip. The delivery tips of the present disclosure are particularly suitable for dispensing a foam medication in conjunction with a squeezable container, a pump container as noted above, or any other suitable container.

Figure 2:
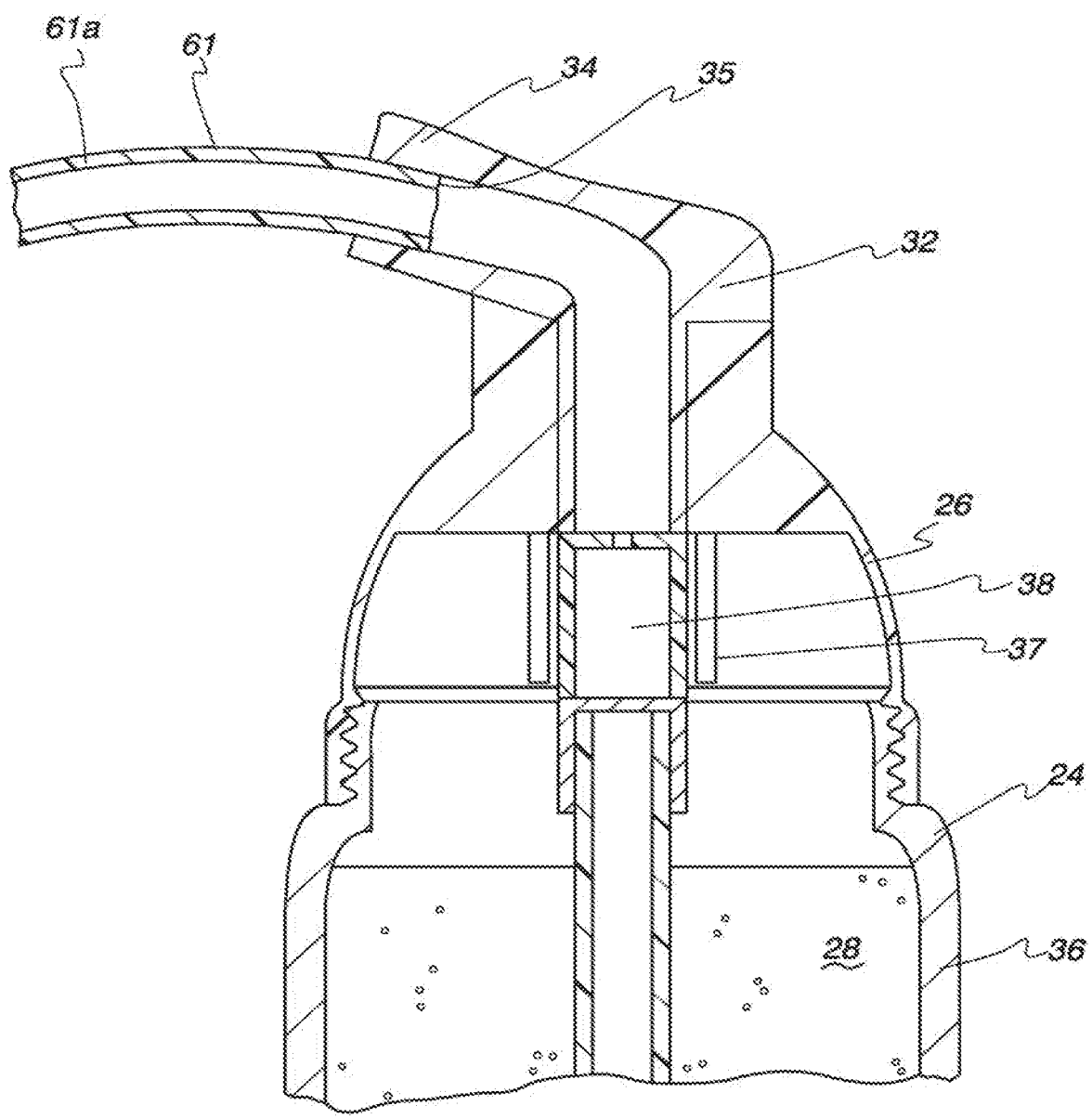
FIG. 2 is a diagrammatic sectional view of the ear medication application apparatus of FIG. 1.
Figures 1, 3A:
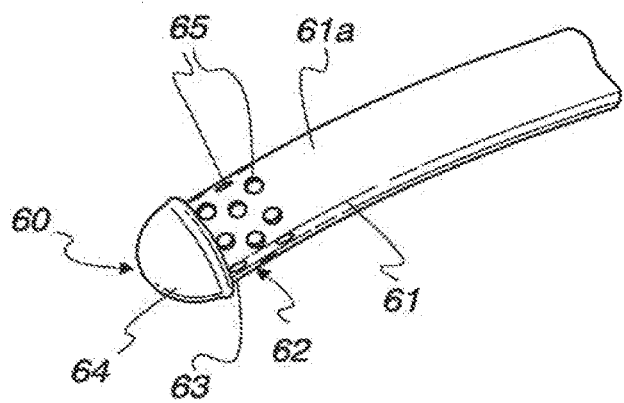
Figures 2, 3A:
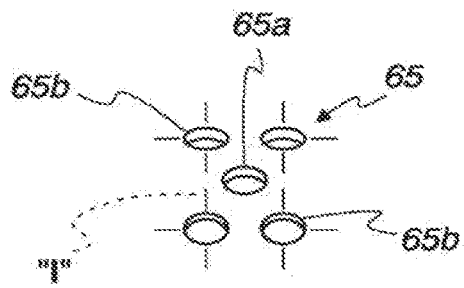

FIG. 3A-1 is a perspective view of a first embodiment of a foam delivery tip 60 constructed in accordance with the principles of the present disclosure. The delivery tip 60 includes an elongated, hollow and cylindrical delivery tube 61 that engages the device 20 such as at a nozzle 34 thereof. The delivery tube 61 has a continuous sidewall 61a and includes a proximal, or mounting end, (not shown) that either fits within a nozzle bore 35 as illustrated in FIG. 2, or otherwise fit the tip of the nozzle 34. In this embodiment, the delivery tip 60 has an opposing distal, or delivery end, 62 with an exposed opening 63 to which a preferably hemispherical-shaped plug 64 can be mated. The plug 64 may be integrally joined to the distal end opening 63 by way of adhesive, plastics welding, ultrasonic welding or any suitable means. Or, the delivery tube may be sealed at its distal with a particular configuration. In the former configuration, it is desirable that the plug tube end be configured, such as by grooves or channels to form multiple points of contact and engagement between the plug 64 and the sidewall of the tube 61 so that the plug 64 will not separate from the tube 61 under pressure. Although the delivery end is illustrated herein as an arcuate one, having hemispherical, ellipsoidal, bulbous configurations and the like, it will be understood that other end configurations may be utilized, such as a blunt end.

In order to provide a means for distributing the foam reliably in the ear, the tube distal end 62 is perforated with a plurality of foam-directing openings 65 that extend radially through the tube sidewall 61a. As used herein "radial" means emanating outwardly along a radius extending from a longitudinal axis of the delivery tube and either perpendicular or at an angle to the longitudinal axis. When viewed from the distal end of the delivery tube, imaginary lines may be drawn through the foam-directing openings 65 to a longitudinal axis and a pattern in a vertical plane, like spokes on a wheel will result. When viewed from above, the imaginary lines drawn through the openings at the distal end may display a similar pattern, but in a horizontal plane.

These foam-directing openings 65 are illustrated in FIG. 3A-2 as a "five-die" pattern, similar to spots on a die cube and wherein one opening 65a is contained within the interior of a multiple-sided imaginary figure "I" formed by connecting the four openings 65b with four imaginary lines 66 as illustrated to the right of FIG. 3A-1. Other suitable patterns may be used such as three outer openings defining an imaginary triangle with a single opening within its boundaries. The placement of the one opening 65a within the imaginary boundaries defined by interconnecting the outer openings 65b ensures the openings 65 will provide 360 degrees of foam coverage around the circumference of the tube distal end 62 in this style embodiment.

Figures 1, 3B:
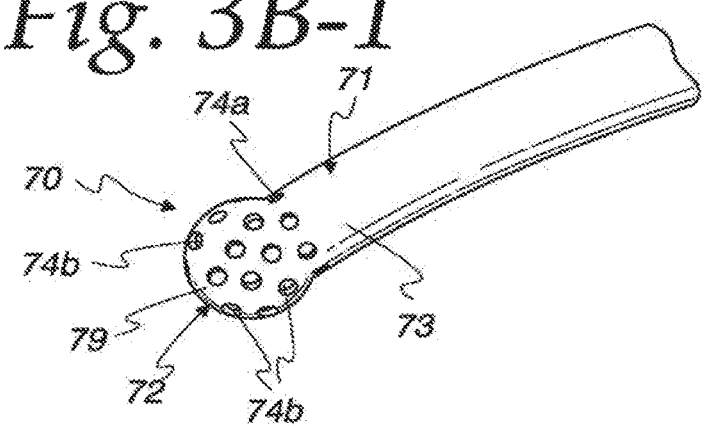
Figures 2, 3B:
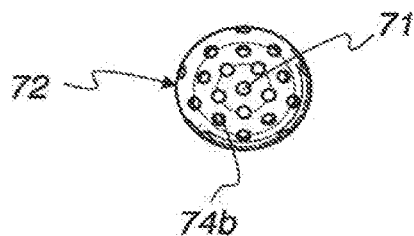

FIG. 3B-1 illustrates a second embodiment of a delivery tip 70 of the present disclosure. This tip 70 will include a hollow tube 71 that may be formed as a seamless structure with a distal delivery end 72 that is continuous, and preferably integrally formed, with the tube sidewall 73. The distal delivery end 72 is shown as generally hemispherical and may have a diameter that is slightly greater than the diameter of the delivery tube 71. The distal delivery end 72 is perforated with a plurality of openings 73 which extend radially into the interior passage of the delivery tube 71. The foam-directing openings 74 have openings 74a that are arranged along the tube sidewall 73 and oriented generally perpendicular to a longitudinal axis of the tube 71.

Figure 4A:
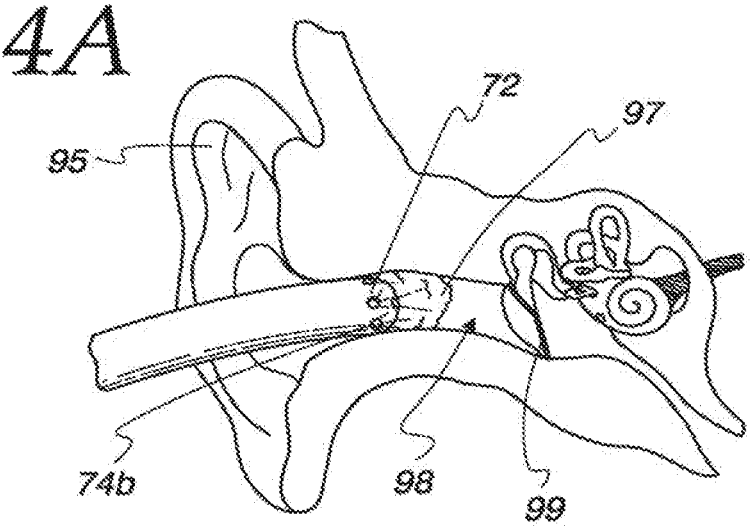
FIG. 4A is a cross-sectional view of a human ear, with the delivery tip of FIG. 3B in place therein.
Figure 4B:
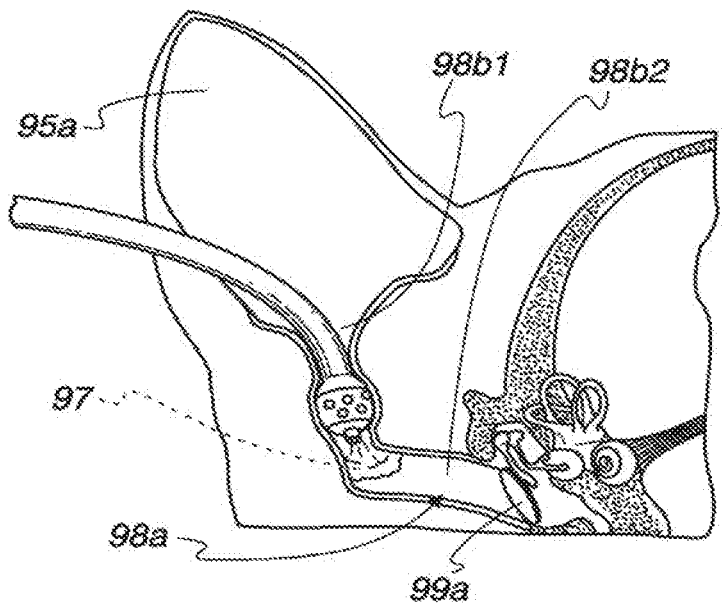
FIG. 4B is cross-sectional view of an animal ear, with the delivery tip of FIG. 8 in place therein.

As illustrated in FIG. 3B-2, other openings 74b are arranged in the hemispherical distal delivery end 72 so as to provide foam passages that are oriented at acute angles and even parallel to the longitudinal axis of the tube 71. In this manner, foam may be introduced both ahead of the distal delivery end 72 (axially) as well as around the tube sidewall 73. The openings 74b may be arranged in a pattern with a single opening aligned with the longitudinal axis of the tube and the other openings arranged in a circular pattern around the center opening. As illustrated in FIG. 4A, the diameter of the distal delivery end 72 is preferably somewhat larger than the overall diameter of an ear canal 98 of a human subject's ear 95 so that the distal delivery end 72 can only be inserted therein a preselected distance from the ear drum 99 to prevent any damaging contact to the ear drum 99 from the distal delivery end 72. The foamed medication 97 exits the delivery end openings 74b and advances into the ear canal under pressure as illustrated in FIG. 4A. FIG. 4B illustrates a cross-section of an animal's ear, such as a dog ear 95a, which has a bifurcated ear canal 98a that leads to an ear drum 99a. This car canal 98a has an initial vertical ear canal section 98b 1 that is joined to an adjacent and subsequent horizontal ear canal section 98b2, which leads to and supports the animal's ear drum 99a.

Figures 1, 3C:
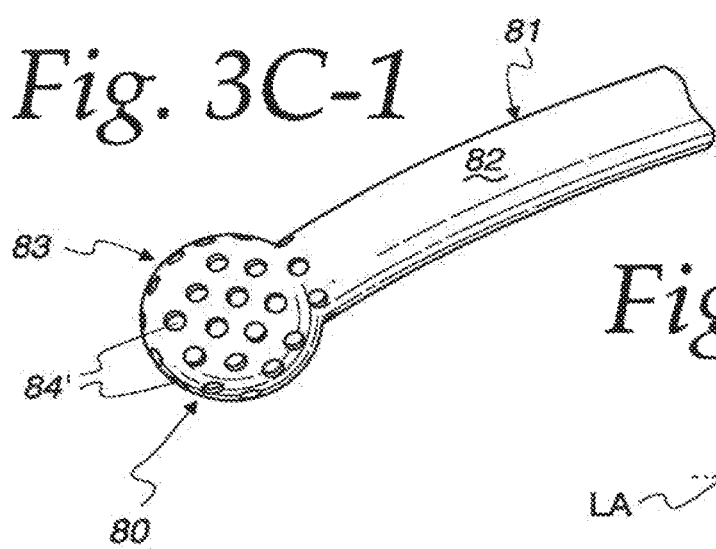
Figures 2, 3C:
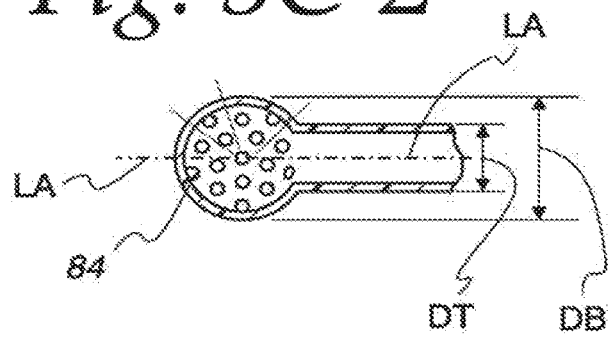

FIG. 3C-1 illustrates a third embodiment of a delivery tip 80 of the present disclosure which includes a hollow, elongated delivery tube 81 defined by a continuous sidewall 82 and having a distal delivery end 83 with a bulbous configuration which is enlarged with respect to the delivery tube 81. In this regard, and as illustrated in FIG. 3C-2, the distal delivery end 83 and tip 80 have an overall diameter DB that is larger than the diameter DT of the delivery tube 81. This enlarged end portion will prevent pushing the distal delivery end 83 of the device too far into the ear canal 98 and middle ear where it may contact the eardrum 99. Additionally, the enlarged distal delivery end 83 provides more surface area than a hemispherical delivery end such as that illustrated in FIG. 3B which means more openings may be provided.

The foam-directing openings 84 in this embodiment are preferably arranged in curved patterns with circular arrays of the openings 84 surrounding the longitudinal axis LA of the delivery tube 81 and also the lead opening 84a which is also usually aligned with the axis LA. The openings 84 in the bulbous distal end 83 are preferably radially disposed with respect to the lead opening 84a and define flow passages that are generally perpendicular to the axis LA so that foam dispensed through the openings 84 is applied in 360 degrees of coverage around the delivery tube 81 and ahead of the tip 80. As can be seen from FIG. 3C-2, the opening arrays have increasing radii as they extend radially outwardly to define almost circular arrangements as shown by the broken lines in the Figure. The openings of an outer circular array tend to be disposed between (but on a separate radius) adjacent openings of an adjacent, interior circular array.

Figure 5:
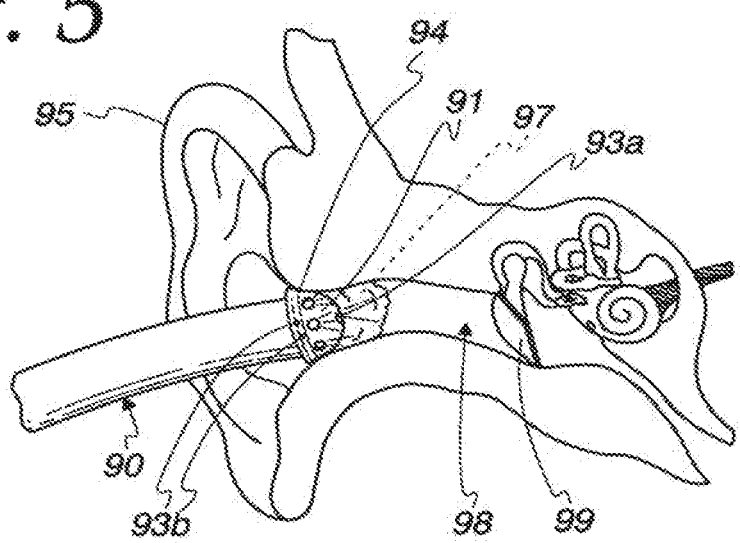
FIG. 5 is an elevational view, partly in section, of another embodiment of a delivery tip for an applicator tube suitable for use with the ear medication applicator of FIG. 1, and in place within an ear canal.

FIG. 5 is a diagrammatic elevational view of another embodiment of a delivery tube 90 with an enlarged distal delivery end 91 that has a skirt, or shoulder, that extends in a circumferential manner to provide a stop surface 92 that contacts the exterior of the ear 95 and prevents the distal delivery end 91 from being forced further into the ear canal 98. The skirt 94 may be continuous or it may be interrupted in its circumferential extent. The enlarged delivery end 91 extends into the ear canal 98 and has openings 93a therein that direct foam into the ear canal. Openings 93b may be formed in the skirt 94 to administer foam medication 97 to the entry area of the ear canal 98.

Figure 6:
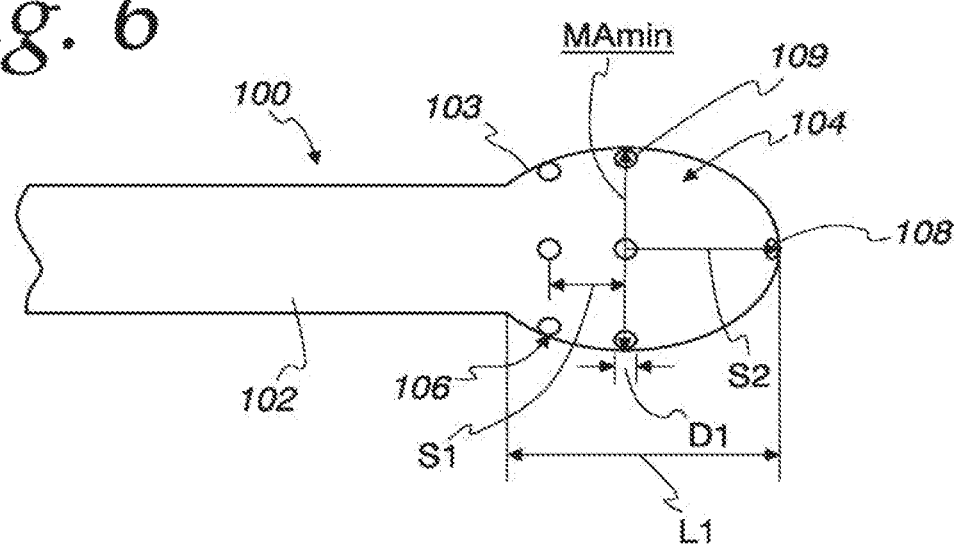
FIG. 6 is a side elevational view of another embodiment of a delivery tip in accordance with the principles of the present invention, with a primary axial foam opening disposed in the distal end of the delivery tip.

FIG. 6 illustrates another embodiment of a delivery tip 100 with an enlarged end in accordance with the present disclosure. The delivery tip 100 includes an elongated delivery tube 102 that terminates at the distal end 103 of the delivery tip in an enlarged end portion 104 that has a bulbous configuration, shown as an ellipsoid, similar to the delivery tip distal end illustrated in FIG. 3C-1. In this embodiment, the enlarged end portion 104 is perforated with a plurality of foam-directing openings 106 that extend completely through the sidewall thereof. The openings 106 include a primary opening 108 that is oriented axially with respect to the end portion 104 and it may be coincident with a longitudinal axis of the delivery tip 100, or not. In any event, the primary opening 108 is disposed in an end surface of the end portion 104, as illustrated. The remaining openings are considered as secondary openings 109 because they are arranged in patterns that are disposed rearwardly of the primary opening 108. The arrays of secondary openings 109 may be separated by a spacing "S1" equal to between about 3 to about 4 diameters (D1) of the openings.

The secondary openings 109 preferably extend in a radial fashion with respect to a longitudinal axis of the delivery tip 100 and they are spaced rearwardly of the primary opening 108. As illustrated in FIG. 6, the secondary openings 109 may be arranged in two circumferential arrays about the longitudinal axis of the enlarged end portion 104, or ellipsoid. The separation distance S2 between the primary and secondary openings 108, 109 is preferably about 5D1 to about 8D1 which is approximately equivalent to about one-third to about one-half of the length L1 of the enlarged end portion 104. This second spacing S2 permits the foam medication to be dispensed through the primary opening 108 forwardly within the ear canal 98 in the direction of the eardrum 99 and through the secondary openings 109 to the surrounding surfaces of the ear canal 98 as shown in FIGS. 4A-4B and 5. This spacing S2 places the secondary openings 109 on the minor axis or on the forwardly curved outer surface, so that the secondary openings open in an perpendicular or forward direction. The forward part of the enlarged end portion 104 will enter the ear canal and only the primary opening 108 will be in a confronting relationship to the eardrum, and thus reduce the likelihood of excessive pressure building up in the ear canal area adjacent the ear drum. While the primary opening 108 fills the ear canal space adjacent to the ear drum with medication, the secondary openings 109 on the circumference of the enlarged end portion 104 and spaced apart from the ear drum 99 will fill the ear canal 98.

Figure 7:
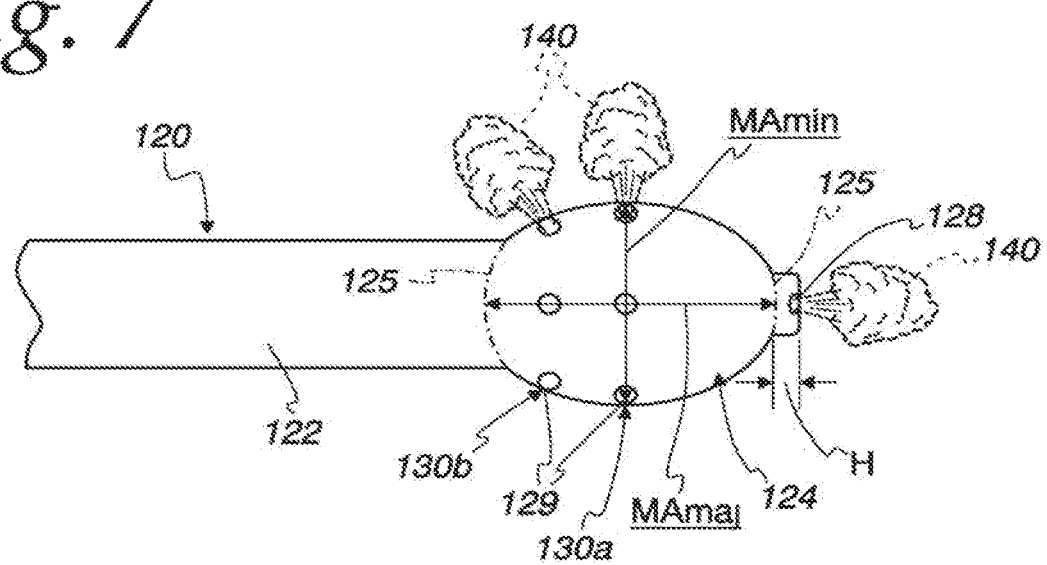
FIG. 7 is a side elevational view of yet another embodiment of a delivery tip similar in configuration to that of FIG. 6, but with an axial extension formed on the distal end of the delivery tip; and, FIG. 8 is an elevational view of another embodiment of a delivery tip similar in configuration to those of FIGS. 6 and 7, but having a barrel-like configuration with an axial extension formed in the distal end of the delivery tip.

FIG. 7 is a side elevational view of a delivery tip 120 which is a variant of the enlarged end delivery tip of FIG. 6. This delivery tip 120 is seen to include a delivery tube 122 that in integrally connected to an enlarged end portion 124 that has a bulbous configuration of an ellipsoid as illustrated. The forward continuation of the outer surface of the enlarged end portion 124 is shown by the dashed lines 125 to the right of FIG. 7. The rear path of the ellipsoid outer surface is shown by the dashed lines 125 in the middle of FIG. 7. The distal end of the delivery tip is configured to include an extension portion 126 that extends axially forwardly of the dashed lines 125 and preferably has a generally cylindrical configuration with an outer diameter less than the outer diameter of the enlarged end portion 124. A primary foam-directing opening 128 is provided in the distal end of the extension portion 126. The extension portions 126 extends past the front dashed line configuration 125 by a distance H of between about 10% and about 30% of the length of the major radius, MAmaj, of the enlarged end portions 124. The extension portion 126 extends the length to which the primary opening 128 will sit within the ear canal 98 and facilitates its orientation within the ear canal 98 in opposition to the car drum 99. The primary opening 128, as noted above directs foam medication into the ear canal 98 in opposition to the ear drum 99. The secondary openings 129 are shown arranged in two circumferential rows, or arrays, 130a, 130b and they are spaced rearwardly of the primary opening 128 (on the extension portion 126) a distance as noted above. The primary and secondary openings 128, 129 therefore extend in two offset directions, one axial and the other radial. In this manner the ear drum and substantially the entire ear canal can be medicated.

Figure 8:
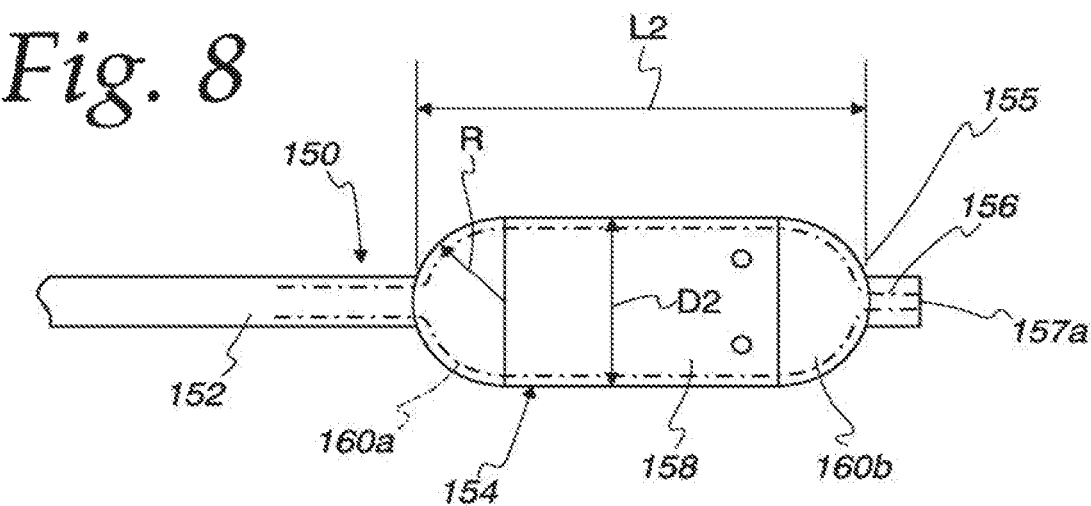

FIG. 8 illustrates yet another embodiment of a delivery tip 150 in accordance with the principles of the present disclosure. This delivery tip 150 is very similar in configuration to the delivery tips of the embodiments of FIGS. 6 and 7, and it includes an elongated, tubular stem portion 152 that communicates with an enlarged end portion 154. A cylindrical or tubular extension portion 156 may be provided at the distal end 155 of the enlarged end portion 154 to define a forward tip of the delivery tube and to support a primary foam-directing opening 157a. This enlarged end portion 154 has a barrel-like configuration with a center tubular or cylindrical barrel section 158 which has a linear extent, when viewed in profile as illustrated in FIG. 8 and which supports a plurality of secondary foam-directing openings 157b. Two end cap sections 160a, 160b are provided and are joined to the center barrel section 158. These end cap sections 160a, 160b are generally hemispherical in shape, having an outer surface that follows (in side profile) a radius R to a point where they meet the stem portion 152 or the forward extension portion 156.

The barrel section 158 has an outer diameter that is greater than that of the stem portion 152 and extension portion 156. This is so that during use, as illustrated in FIG. 4B, the delivery tip 150 will contact the surrounding area of the ear canal 98a at a location that prevents the extension portion 156 from impacting on the eardrum 99a of the subject, whether it be an animal or human subject. The extension portion 156 and the primary opening 157a thereof project a bit past the distal end of the enlarged end portion 154. This configuration is particularly useful in use of the device with animals, as most animals, as illustrated in FIG. 4B, have an ear canal 98a that has two distinct sections, such as the initial vertical ear canal section 98b1 and an adjacent, subsequent horizontal ear canal portion 98b2 in which the eardrum 99a is disposed. The enlarged end portion 154 is preferably sized to fit in the vertical ear canal 98b1 section up or proximate to the junction of the vertical and horizontal ear canal sections. The extension portion 156 thereupon projects forwardly to direct its primary opening 157a into the horizontal ear canal section 98b2, while the secondary openings 157b are directed around the circumference of the enlarged end portion 156 into the vertical ear canal section 98b1 and against the wall(s) of the ear canal 98a that make up the vertical ear canal section 98b1. Thus the delivery tip 150 is capable of delivering a foam medication in two different directions.

The enlarged end portion 154 preferably has an aspect ratio (L/D) of between about 1.4 to about 4, where L is the length L2 of the enlarged end portion, in FIG. 8 and D is the outer diameter D2 of the enlarged end portion 154. Such an aspect ratio also applies to the other enlarged end portions illustrated in FIGS. 6 and 7, and it will be understood that this range is preferred, as other ratios may provide reliable dispensing depending on the overall diameter of the ear canal, particularly in animals, where the diameter of the proximal area of the ear canal can range from about 2 mm to about 3.6 mm. A more preferred range of aspect ratios for use is about 1.4 to about 2.5, usually with the units in millimeters. The secondary foam-directing openings 157*b* are preferably spaced evenly around the circumference of the enlarged end barrel section 158, and preferably are located at even intervals of 90 degrees in their array. As shown in FIG. 4B, it can be seen that the enlarged end portion 154 can traverse most, if not all of an animal's vertical ear canal section 98*b*1 so that the extension portion 156 and/or the primary opening 157*a* extends or is directed into the horizontal ear canal section 98*b*2. The size of the enlarged end portion 154 inhibits the delivery tube from making the turn into the horizontal ear canal 98*b*2 and contacting the ear drum 99*a*. In this manner, foam medication will be dispensed into both the vertical and horizontal ear canal sections of the animal, respectively through the secondary and primary foam-directing openings 157*b*, 157*a*.

It can be seen that delivery tips and devices in accordance with the present disclosure provide advantages for the administering of foam medications in human and animal ears. The openings are positioned to direct the foam around and ahead of the end of the delivery tube, as shown by the puffs of foam 140 in FIGS. 6 and 7. The tubes may be made of a hypo-allergenic material and discarded after use so as to eliminate the need for keeping the delivery tube end out of contact with unsterilized surfaces.

While preferred embodiments have been shown and described, it is envisioned that those skilled in the art may devise various modifications without departing from the spirit and scope of the foregoing Description and the appended Claims.

What is claimed is:

1. A foam medication dispensing apparatus for use in treatment of conditions within a subject's ears, said foam medication dispensing apparatus comprising:
    (1) a container having a medication reservoir adapted to contain foamable medication;
    (2) a nozzle supported by said container in communication with said reservoir and providing a flowpath for said foamable medication out of said container;
    (3) a hollow delivery tube, said delivery tube being defined by an outer wall, said delivery tube having:
        (i) a proximal end operatively connected to said nozzle to define a flowpath for said foamable medication from said medication reservoir to a subject's ear canal, said subject's ear canal including a vertical ear canal section and a horizontal ear canal section; and
        (ii) a distal delivery end opposite to said proximal end, said delivery tube outer wall including a set of foam-directing openings extending therethrough and arranged near said distal delivery end, said set of foam-directing openings defining a set of individual flowpaths communicating between said delivery tube and a surrounding area of said subject's ear when said distal delivery end is inserted into said subject's ear, said set of foam-directing openings including a primary foam-directing opening adapted to release said foamable medication into said horizontal ear canal section; and,
    (4) wherein
        (iii) said distal delivery end has an enlarged end portion having a barrel-like configuration;
        (iv) said barrel-like configuration has an outer diameter that is larger than an outer diameter of said delivery tube;
        (v) said primary foam-directing opening is disposed on said distal end of said delivery tube and aligned with a longitudinal axis of said delivery tube; and
        (vi) said barrel-like configuration is adapted to fit into said vertical ear canal section; and,
        (vii) said barrel-like configuration inhibits said delivery tube from making a turn into said horizontal ear canal section when inserted into said subject's ear canal.

2. The foam medication dispensing apparatus of claim 1 wherein said barrel-like configuration has an aspect ratio of L/D of between about 1.4 to about 4, where L is the length of said barrel-like configuration and D is the outer diameter of said barrel-like configuration.

3. The foam medication dispensing apparatus of claim 2 wherein said barrel-like configuration has an aspect ratio of L/D of between about 1.4 to about 2.5, where L is the length of said barrel-like configuration and D is the outer diameter of said barrel-like configuration.

4. The foam medication dispensing apparatus of claim 2 wherein said distal end further includes an extension portion extending forward from said barrel-like configuration and supporting said primary foam-directing opening.

5. The foam medication dispensing apparatus of claim 4 wherein said outer diameter of said barrel-like configuration is larger than an outer diameter of said extension portion.

6. The foam medication dispensing apparatus of claim 5 wherein said extension portion is cylindrical or tubular.

7. The foam medication dispensing apparatus of claim 5 wherein said set of foam-directing openings further includes a subset of secondary foam-directing openings arranged on said barrel-like configuration, said subset of secondary foam-directing openings adapted to release said foamable medication into said vertical ear canal section.

8. The foam medication dispensing apparatus of claim 7 wherein said subset of secondary foam-directing openings are arranged in at least one array which is spaced rearwardly of said primary foam-directing opening such that said primary and said subset of secondary foam-directing openings are offset from each other.

9. The foam medication dispensing apparatus of claim 7 wherein said subset of secondary foam-directing openings are arranged in a circumferential array.

10. The foam medication dispensing apparatus of claim 2 wherein said set of foam-directing openings further includes a subset of secondary foam-directing openings arranged on said barrel-like configuration, said subset of secondary foam-directing openings adapted to release said foamable medication into said vertical ear canal section.

11. The foam medication dispensing apparatus of claim 10 wherein said subset of secondary foam-directing openings are arranged in at least one array which is spaced rearwardly of said primary foam-directing opening such that said primary and said subset of secondary foam-directing openings are offset from each other.

12. The foam medication dispensing apparatus of claim 10 wherein said subset of secondary foam-directing openings are arranged in a circumferential array.

* * * * *